United States Patent [19]

Schoen et al.

[11] Patent Number: 4,912,113
[45] Date of Patent: Mar. 27, 1990

[54] 3,7-DIAZABICYCLO(3,3,1)NONANE COMPOUNDS AND PHARMACEUTICAL COMPOSITIONS CONTAINING SUCH COMPOUNDS

[75] Inventors: Uwe Schoen, Burgdorf; Wolfgang Kehrbach; Gerd Buschmann, both of Hanover; Ulrich Kuhl, Gehrden; Dieter Ziegler, Ronnenberg, all of Fed. Rep. of Germany

[73] Assignee: Kali-Chemie Pharma GmbH, Hanover, Fed. Rep. of Germany

[21] Appl. No.: 239,766

[22] Filed: Sep. 2, 1988

[30] Foreign Application Priority Data

Sep. 9, 1987 [DE] Fed. Rep. of Germany ....... 3730222
Sep. 9, 1987 [DE] Fed. Rep. of Germany ....... 3730224

[51] Int. Cl.$^4$ .................. A61K 31/44; C07D 471/08; C07D 471/10
[52] U.S. Cl. .................................... 514/278; 514/300; 546/18; 546/122
[58] Field of Search .................. 546/122, 18; 514/300, 514/278

[56] References Cited

U.S. PATENT DOCUMENTS 3,962,449 6/1976 Binnig et al. ......................... 424/267
4,183,935 1/1980 Binnig et al. ......................... 424/256
4,550,112 10/1985 Schoen et al. ....................... 514/278

FOREIGN PATENT DOCUMENTS 2658558 6/1978 Fed. Rep. of Germany .

OTHER PUBLICATIONS

Hoerlein, Eur. J. Med. Chem., 12, No. 4, pp. 301-305 (1977).

Primary Examiner—Mary C. Lee
Assistant Examiner—Barry Dentz
Attorney, Agent, or Firm—Foley & Lardner, Schwartz, Jeffery, Schwaab, Mack, Blumenthal & Evans

[57] ABSTRACT

3,7-Diazabicyclo[3,3,1]nonane compounds having valuable heart rate-affecting pharmacological properties corresponding to the Formula I:

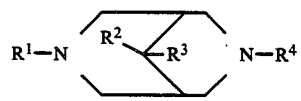

wherein
$R^1$ is alkyl, cycloalkylalkyl or benzyl,
$R^2$ is lower alkyl,
$R^3$ is lower alkyl, or
$R^2$ and $R^3$ together form an alkylene chain, and
$R^4$ represents a benzhydryl group, optionally substituted by halogen, lower alkoxy, lower alkyl, hydroxy or trifluoromethyl, or a cinnamyl group optionally substituted by halogen, lower alkyl, lower alkoxy, hydroxy, nitro or trifluoromethyl.

5 Claims, No Drawings

3,7-DIAZABICYCLO(3,3,1)NONANE COMPOUNDS AND PHARMACEUTICAL COMPOSITIONS CONTAINING SUCH COMPOUNDS

BACKGROUND OF THE INVENTION

This invention relates to new 3-benzhydryl-and 3-cinnamyl-3,7-diazabicyclo[3,3,1]nonane compounds and their salts, to pharmaceutical compositions containing such compounds, and to a method and intermediate products for producing such compounds.

West German No. DE-OS 26 58 558 discloses 3-alkanoyl- and 3-aroyl-3,7-diazabicyclo[3,3,1]nonane compounds having analgesic activity. U.S. Pat. No. 3,962,449 discloses 3,7-diazabicyclo[3,3,1]nonane derivatives substituted in the 3- and 7- positions by alkyl or phenylalkyl groups and having antiarrhythmic properties. 7-Benzyl-3-phenylalkyl-3,7-diazabicyclo-[3,3,1]nonane derivatives, likewise having antiarrhythmic activity, are described in U.S. Pat. No. 4,183,935. Additional 3,7-diazabicyco[3,3,1]nonane derivatives with antiarrhythmic properties are known from U.S. Pat. No. 4,550,112.

SUMMARY OF THE INVENTION

It is the object of the present invention to provide new 3,7-diazabicyclo[3,3,1]nonane compounds with valuable pharmacological properties.

It is a particular object of the invention to provide new compounds with favorable heart rate-lowering and/or antiarrhythmic activity.

It is also an object of the invention to provide new pharmaceutical compositions incorporating 3,7-diazabicyclo[3,3,1]nonane compounds, a new method for producing such compounds, and new intermediate compounds useful in their production.

These and other objects of the invention are achieved in accordance with the present invention by providing a compound corresponding to the Formula I:

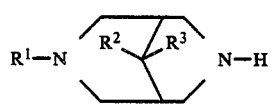

wherein
  $R^1$ is an alkyl group with 1–6 carbon atoms, a cycloalkylalkyl group with 4–9 carbon atoms or a benzyl group,
  $R^2$ is lower alkyl,
  $R^3$ is lower alkyl, or
  $R^2$ and $R^3$ together form an alkylene chain with 3–6 carbon atoms, and
  $R^4$ is a benzhydryl group corresponding to the Formula a:

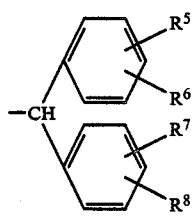

wherein
  $R^5$ is hydrogen, halogen, lower alkoxy, lower alkyl, hydroxy or trifluoromethyl,
  $R^6$ is hydrogen, lower alkyl, halogen or lower alkoxy,
  $R^7$ is hydrogen, halogen, lower alkyl, lower alkoxy, hydroxy or trifluoromethyl, and
  $R^8$ is hydrogen, lower alkyl, halogen or lower alkoxy, or
  $R^4$ is a cinnamyl group corresponding to the Formula b:

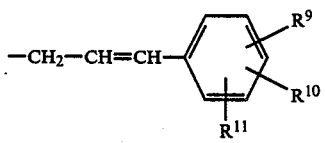

wherein
  $R^9$ is hydrogen, halogen, lower alkyl, lower alkoxy or hydroxy,
  $R^{10}$ is hydrogen, halogen, lower alkoxy, lower alkyl, hyroxy or, if $R^9$ is hydrogen, $R^{10}$ may also be trifluoromethyl or nitro, and
  $R^{11}$ is hydrogen, or, if $R^9$ and $R^{10}$ are lower alkoxy, $R^{11}$ may also be lower alkoxy,
or an acid addition salt thereof.

According to a further aspect of the invention, the foregoing compounds are produced by a method comprising:

(a) reacting a compound corresponding to the Formula II:

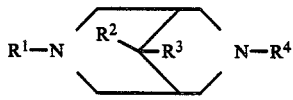

wherein $R^1$, $R^2$ and $R^3$ have the above meanings, with a compound corresponding to the Formula III:

$$R^{4'}\text{—X} \qquad \text{III}$$

wherein $R^{4'}$ has the meaning given above for $R^4$ except that any free hydroxy groups are provided with a protective group, and X is an aminolytically cleavable group, or (b) to produce a compound corresponding to the Formula Ia:

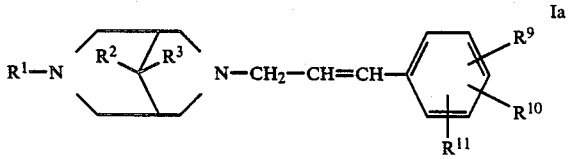

wherein $R^1$, $R^2$, $R^3$, $R^9$, $R^{10}$ and $R^{11}$ have the above meanings, reducing a compound corresponding to the Formula XIV:

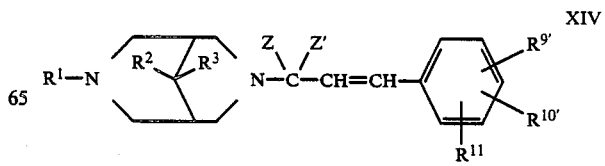

where $R^1$, $R^2$, $R^3$ and $R^{11}$ have the above meanings, $R^{9'}$ and $R^{10'}$ have the meanings given above for $R^9$ and $R^{10}$ except that any free hydroxy groups are provided with a protective group and Z and Z' together are oxygen, or Z represents hydroxy and Z' hydrogen, and subsequently splitting off any hydroxy protecting groups.

According to a further preferred aspect of the invention, a compound is provided corresponding to the Formula XIV':

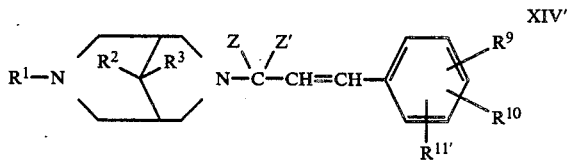

XIV' wherein
- $R^1$ is an alkyl group with 1–6 carbon atoms, a cycloalkylalkyl group with 4–9 carbon atoms or a benzyl group,
- $R^2$ is lower alkyl,
- $R^3$ is lower alkyl, or
- $R^2$ and $R^3$ together form an alkylene chain with 3–6 carbon atoms,
- $R^9$ is hydrogen, halogen, lower alkyl or lower alkoxy,
- $R^{10}$ is hydrogen, halogen, lower alkoxy, lower alkyl or, if $R^9$ is hydrogen, $R^{10}$ may also be trifluoromethyl or nitro,
- $R^{11'}$ is hydrogen or, if $R^9$ and $R^{10}$ are lower alkoxy and $R^2$ and $R^3$ are lower alkyl, $R^{11}$ may also be lower alkxoy, and
- Z and Z' together represent oxygen, or Z represents hydroxy and Z' hydrogen, or an acid addition salt thereof.

DETAILED DESCRIPTION OF PREFERRED EMBODIMENTS

In accordance with the present invention it has been found that 3,7-diazabicyclo[3,3,1]nonane compounds substituted in the 3-position by a benzhydryl group or a cinnamyl group possess valuable pharmacological properties, in particular valuable properties having an effect on the heart. They are characterized by a favorable activity profile with heart rate-lowering effects and antiarrhythmic propeties.

The present invention therefore relates to new 3,7-diazabicyclo[3,3,1]nonane compounds corresponding to the general Formula I:

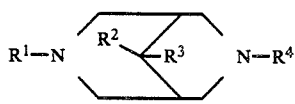

I wherein
- $R^1$ is an alkyl group with 1–6 carbon atoms, a cycloalkylalkyl group with 4–9 carbon atoms or benzyl,
- $R^2$ is lower alkyl,
- $R^3$ is lower alkyl, or
- $R^2$ and $R^3$ together form an alkylene chain with 3–6 carbon atoms, and
- $R^4$ is a benzhydryl group of the general Formula a:

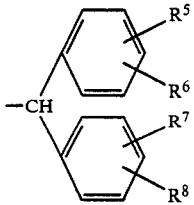

a wherein
- $R^5$ is hydrogen, halogen, lower alkoxy, lower alkyl, hydroxy or trifluoromethyl,
- $R^6$ is hydrogen, lower alkyl, halogen or lower alkoxy,
- $R^7$ is hydrogen, halogen, lower alkyl, lower alkoxy, hydroxy or trifluoromethyl, and
- $R^8$ is hydrogen, lower alkyl, halogen or lower alkoxy, or
- $R^4$ is a cinnamyl group of the general Formula b:

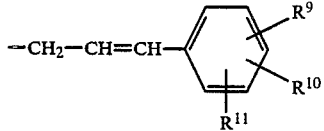

b wherein
- $R^9$ is hydrogen, halogen, lower alkyl, lower alkoxy or hydroxy,
- $R^{10}$ is hydrogen, halogen, lower akoxy, lower alkyl, hydroxy or, if $R^9$ is hydrogen, $R^{10}$ may also be trifluoromethyl or nitro, and
- $R^{11}$ is hydrogen, or, if $R^9$ and $R^{10}$ are lower alkoxy, $R^{11}$ may also be lower alkoxy, or an acid addition salt thereof.

If in the compounds of Formula I, $R^1$ represents an alkyl group, it may be straight-chain or branched and contain 1 to 6, preferably 2 to 4, carbon atoms. A cycloalkylalkyl group $R^1$ may contain 4 to 9, preferably 4 to 7, carbon atoms. Alkyl and cycloalkylakyl groups, particularly branched groups, have proved to be particularly suitable $R^1$ groups.

If the substituents $R^2$ and $R^3$ represent lower alkyl, these alkyl groups may be straight-chain or branched and contain 1 to 4, preferably, 1 to 3, carbon atoms. The alkyl groups $R^2$ and $R^3$ are advantageously of the same type, but may also be different. If $R^2$ and $R^3$ together form an alkylene chain, this may contain 3 to 6, preferably, 4 to 5, carbon atoms.

In the compounds of Formula I the $R^4$ group may represent an optionally substituted benzhydryl group a. If the substituents $R^5$ to $R^8$ of the benzhydryl group a represent or contain lower alkyl groups, these may contain 1 to 4, particularly 1 to 2, carbon atoms. Halogen substituents $R^5$ to $R^8$ preferably represent fluorine or also chlorine. Preferably the benzhydryl group $R^4$ contains in total only 0–2 substituents. The groups $R^5$ and $R^7$ preferably represent hydrogen, halogen, particulary fluorine, or also lower alkyl, particularly methyl. the substituents $R^6$ and $R^8$ preferably represent hydrogen or also lower alkyl, particularly methyl.

In the compounds of Formula I the group $R^4$ may also represent an optionally substituted cinnamyl group b. If the substituents $R^9$ to $R^{11}$ of the cinnamyl group b represent or contain lower alkyl groups, these may contain 1 to 4, particularly 1 or 2, carbon atoms. Halogen substituents $R^9$ and/or $R^{10}$ preferably represent chlorine. Preferably the cinnamyl group $R^4$ is unsubstituted or monosubstituted or also disubstituted by halogen or methoxy.

According to the invention, the new 3,7-diazabicyclo[3,3,1]nonane compounds of Formula I and their acid addition salts are obtained (a) by reacting compounds of the general Formula II:

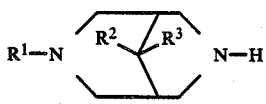
II in which $R^1$, $R^2$ and $R^3$ have the above meanings, with compounds of the general Formula III:

$R^{4'}—X$
III in which $R^{4'}$ has the meaning given above for $R^4$, except that any free hydroxy groups are provided with a protective group, and X is an aminolytically cleavable group, or (b) to produce compounds of the general Formula Ia:

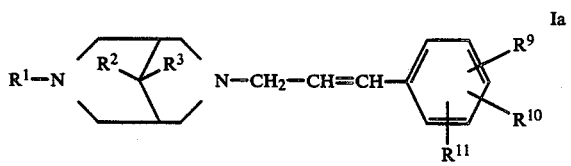
Ia in which $R^1$, $R^2$, $R^3$, $R^9$, $R^{10}$ and $R^{11}$ have the above meanings, by reducing compounds of the general Formula XIV:

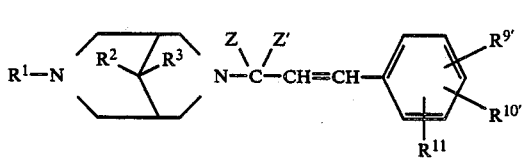
XIV in which $R^1$, $R^2$, $R^3$ and $R^{11}$ have the above meanings, $R^{9'}$ and $R^{10'}$ have the meanings given above for $R^9$ and $R^{10}$, but with any free hydroxy groups being provided with a protective group, and Z and Z' together are oxygen, or Z represents hydroxy and Z' hydrogen, and subsequently removing any hydroxy protecting groups, or if desired, in compounds of Formula I in which $R^4$ represents a methoxy-substituted benzhydryl group, converting the methoxy substituents into hydroxy groups, and if desired, converting free compounds of Formula I into their acid addition salts, or converting the acid addition salts into the free compounds of Formula I.

The reaction of compounds of Formula II with compounds of Formula III may be carried out in a known way under standard conditions for alkylation of amines. Thus, the reaction may be advantageously carried out under basic conditions in an organic solvent which is inert under the reaction conditions. Preferred aminolytically cleavable groups in the compounds of Formula III include halogens, such as chlorine or bromine, or also organic sulfonic acid groups, for instance, residues of lower alkane sulfonic acids such as methane sulfonic acid or of aromatic sulfonic acids such as benzene sulfonic acids or lower alkyl-substituted or halogen-substituted benzene sulfonic acids, e.g., toluene sulfonic acid or bromobenzene sulfonic acid. In particular, aprotic solvents such as ethers, particularly cyclic ethers such as tetrahydrofuran, dimethylformamide, aromatic hydrocarbons such as benzene or toluene, or mixtures of the aforementioned solvents are suitable as inert organic solvents. Advantageously, the reaction is carried out in the presence of at least an equivalent quantity of a base. Examples of suitable bases include alkali metal carbonates, alkali metal amides, alkali metal hydrides, and organo-lithium compounds such as lower alkyl lithium or phenyl lithium. Thus, for example, the use of potassium carbonate in dimethylformamide or of n-butyl lithium in tetrahydrofuran or of lithium amide in tetrahydrofuran or dimethylformamide has proved advantageous. The reaction temperature may vary according to the type of base used, and is advantageously selected between about 0° C. and the boiling temperature of the solvent, in particular, between approximately 0° C. The duration of the reaction may be between 2 and 12 hours depending on the type of reaction conditions selected.

If the $R^{4'}$ group of the compounds of Formula III contains free hydroxy substituents, these must be protected in a known way during the reaction with the compounds of Formula II by protective groups which can easily be removed again. Suitable protective groups for phenolic OH groups which can easily be split off again after the reaction are known, e.g., from E. McOmie, *Protective Groups in Organic Chemistry*, Plenum Press (1971). For instance, esters, e.g., acetates; easily cleavable ethers, particularly tetrahydropyranyl ethers; or easily cleavable carbonates, such as benzyl carbonate, are suitable for protecting a hydroxyl group. If $R^{4'}$ is a cinnamyl group substituted by hydroxy, protective groups must be selected which are easy to subsequently remove under conditions under which the double bond of the cinnamyl group is not attacked.

The reduction of compounds of Formula XIV according to process variant b may take place in accordance with standard methods for reducing amides and aminocarbinols. Complex metal hydrides are suitable as reduction agents. Thus, for example, complex aluminum hydrides, such as lithium aluminum hydride or sodium-bis-(2-methoxyethoxy)-dihydroaluminate in a solvent which is inert under the reaction conditions, for instance, an open-chained or cyclic ether such as diethyl ether or tetrahydrofuran, optionally in a mixture with aromatic hydrocarbons such as benzene or toluene, are suitable for the reduction of amides of Formula XIV. Furthermore, sodium borohydride is also suitable for the reduction of amino carbinols of Formula XIV. The reduction with sodium borohydride may take place in a lower alcohol, for instance, methanol, optionally in a mixture with other inert organic solvents. The reaction temperature may vary according to the type of reducing agent used. Temperatures of between 0° C. and room temperature are advantageous.

Compounds of Formula I in which $R^4$ represents a benzyl group a containing free hydroxy substituents, may be obtained from appropriate methoxy-substituted compounds of Formula I by cleavage of the ether groups. The freeing of the hydroxy group may take place according to standrd methods for cleaving phenolic ethers. For instance, a suitable technique is to cleave the ether groups by treating the compounds with hydriodic acid in a solvent which is inert under the reaction conditions.

The compounds of Formula I may be isolated from the reaction mixture and purified by known techniques. Acid addition salts may be converted into the free bases in the usual way, and the latter converted in a known way into pharmacologically acceptable acid addition salts if desired. Salts of the compounds of Formula I with inorganic acids, e.g., hydrogen halide acids, especially hydrochloric acid, sulfuric acid or phosphoric acids, or with organic acids, for example lower aliphatic monocarboxylic or dicarboxylic acids such as lactic acid, maleic acid, fumaric acid, tartaric acid or acetic acid, or sulfonic acids, for example lower alkyl sulfonic acids such as methane sulfonic acid or benzenesulfonic acids optionally substituted in the benzene ring by halogen or lower alkyl such as p-toluene sulfonic acid or cyclohexylamino sulfonic acid, for example, are suitable as pharmacologically acceptable acid addition salts of such compounds.

$R^2$ and $R^3$ are different, the compounds may exist in two stereoisomeric forms. The present invention comprises both the isomer mixtures and the pure isomers of these compounds of Formula I. Isomer mixtures may be separated by known techniques into the individual isomers either as final compounds or at an intermediate product stage, for example, by fractional crystallization or by separation using column chromatography.

If $R^4$ represents an optionally substituted cinnamyl group b, this group may have a cis-configuration or trans-configuration.

The 3,7-diazabicyclo[3,3,1]nonane compounds of Formula II used as starting compounds are known from U.S. Pat. No. 4,550,112 and West German DE-OS 26 58 558, and/or may be produced in a known manner in accordance with, or analagously to, the methods described in these documents. For example, compounds of Formula II may be obtained by splitting off the benzyl group $R^{12}$ from compounds of Formula IV:

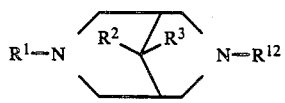

IV wherein $R^1$, $R^2$ and $R^3$ have the above meanings and $R^{12}$ is benzyl by hydrogenolysis in a known manner. The hydrogenolytic cleavage of the $R^{12}$ group may be effected with hydrogen in the presence of a palladium/carbon catalyst in an organic, protic, polar solvent, for example a lower alcohol such as ethanol, advantageously in catalytic quantities of glacial acetic acid. Hydrogenation may advantageously be carried out at room temperature and a hydrogen pressure of approximately 5 to 6 atmospheres.

Starting compounds of Formula IV can be obtained, for example, starting from tetraoxo compounds of Formula V:

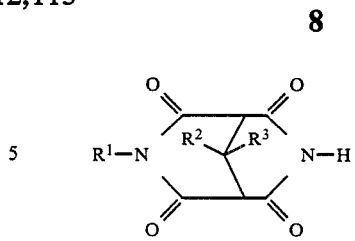

V wherein $R^1$, $R^2$ and $R^3$ have the above meanings. For this purpose the tetraoxo compounds of Formula V are first reacted with benzyl halides of Formula VI:

$R^{12}$—Hal    VI in which $R^{12}$ has the above meaning and Hal represents halogen, particularly chlorine or bromine, to produce N,N'-disubstituted tetraoxo compounds of Formula VII,

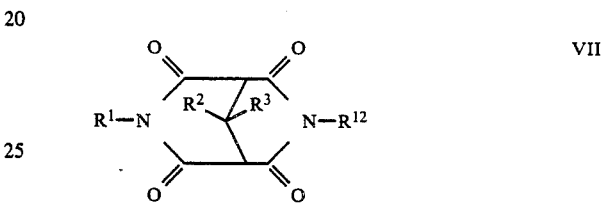

VII in which $R^1$, $R^2$, $R^3$ and $R^{12}$ have the above meanings, and subsequently reducing the compounds of Formula VII to the compounds of Formula IV.

The reaction of the diimide compounds of Formula V with the compounds of Formula VI may take place according to usual methods for alkylating imides. The reaction advantageously takes place in a solvent which is inert under the reaction conditions in the presence of a base at an elevated temperature, for instance the boiling temperature of the solvent. Thus, for example, alkali metal carbonates, amides or hydrides in dimethyl formamide, or alkali metal alcoholates in a lower alcohol are suitable. Benzyl halide is used advantageously in excess.

The 2,4,6,8-tetraoxo-3,7-diazabicyclo[3,3,1]nonane compounds of Formula V are known and/or can be produced according to the method described by Hoerlein (Eur. J. Med. Chem., 12, 301–305) by ring closure of 2,6-dioxo-3,5-dicyanopiperidine compounds of Formula VIII:

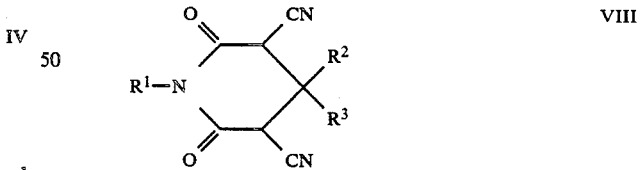

VIII wherein $R^1$, $R^2$ and $R^3$ have the above meanings, in high-percentage acid/water mixtures. The 2,6-dioxo-3,5-cyanopiperidines VIII are themselves obtained in a known way by condensation of correspondingly substituted alkylidene cyanoacetic esters of Formula IX, $$\begin{array}{c} CN \quad R_2 \\ | \quad / \\ C=C-R^3 \\ | \\ COOC_2H_5 \end{array} \quad IX$$

in which $R^2$ and $R^3$ have the above meanings, with cyanoacetic amides of Formula X,

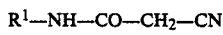

in which $R^1$ has the above meaning.
Compounds of Formula IIa:

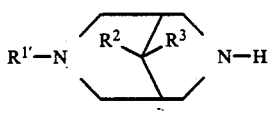

IIa in which $R^2$ and $R^3$ have the above meanings and $R^{1'}$ has the meaning given for $R^1$ with the exception of benzyl, may also be obtained by alkylating compounds of Formula II in which $R^1$ is benzyl, with compounds of Formula XI:

XI in which $R^{1'}$ and X have the above meanings, and subsequently cleaving the benzyl group by hydrogenolysis. The alkylation takes place in a known way, e.g., under the conditions given above for the reaction of compounds of Formula II with compounds of Formula III.

Compounds of Formula XIV':

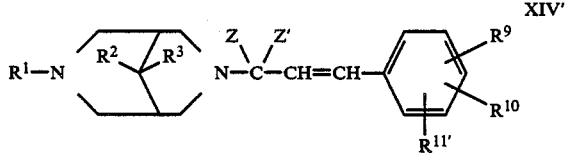

XIV' in which $R^1$, $R^2$, $R^3$, $R^9$, $R^{10}$, Z and Z' have the meanings given above, and $R^{11'}$ is hydrogen, or, if $R^9$ and $R^{10}$ are lower alkoxy and $R^2$ and $R^3$ are lower alkyl independently of each other, $R^{11'}$ may also be lower akoxy, have not previously been described in the literature. According to the invention, the compounds of Formula XIV' represent valuable intermediate products for the production of pharmacologically active compounds, for instance compounds of Formula I.

The amides of Formula XIVa:

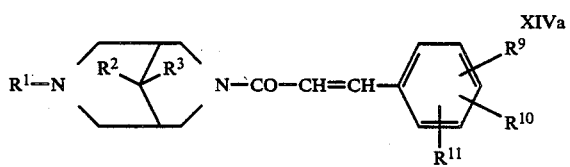

XIVa in which $R^1$, $R^2$, $R^3$, $R^9$, $R^{10}$ and $R^{11}$ have the above meanings, may be obtained in a known way by reacting acids of the Formula XV,

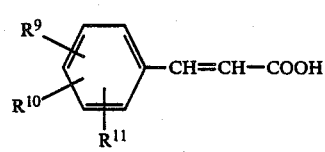

XV in which $R^9$, $R^{10}$ and $R^{11}$ have the above meanings, or their reactive acid derivatives, with compounds of Formula II. The reaction of acids of Formula XV and their reactive derivatives with compounds of Formula II may be carried out according to standard methods for the formation of amides by aminoacylation. Advantageously, the acids are activated in a known way be conversion into a reactive derivative. For example, acid halides, in particular chlorides or bromides, lower alkyl esters or mixed anhydrides, e.g., anhydrides with lower alkane carboxylic acids or lower alkane sulfonic acids, in particular acetic acid or methane sulfonic acid, are suitable as reactive acid derivatives. Thus compounds of Formula XVa:

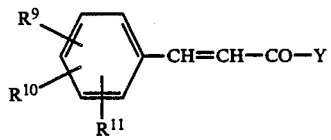

XVa in which $R^9$, $R^{10}$ and $R^{11}$ have the above meanings and Y is hydroxy, lower alkoxy, halogen or an acyloxy group —OY', wherein Y' represents lower alkyl carbonyl or lower alkyl sulfonyl, are suitable for reaction with the compounds of Formula II.

The conversion of free acids of Formula XV into reactive acid derivatives takes place in a known way. Thus acid halides of Formula XVa may be obtained, for example, by reacting the acids of Formula XV with a halogenating agent, for instance phosphorus trichloride, phosphorus pentabromide or thionyl chloride. If desired, the reaction may be carried out in the presence of pyridine or another tertiary organic base. Mixed acid anhydrides may be obtained, for example, by reacting acids of Formula XV or their alkali metal salts with an appropriate organic acid chloride in an organic solvent which is inert under the reaction conditions, for instance, a halogenated hydrocarbon, optionally in the presence of a tertiary organic base, such as pyridine.

The reaction of the acid derivatives of Formula XVa with the compounds of Formula II may take place in a solvent which is inert under the reaction conditions at temperatures of between $-30°$ C. and the boiling temperature of the solvent. Halogenated hydrocarbons such as dichloromethane or chloroform, aromatic hydrocarbons such as benzene or toluene, cyclic ethers such as tetrahydrofuran or dioxane or mixtures of these solvents are suitable as solvents. If desired, the reaction may be carried out in the presence of a neutralizing reagent. Inorganic bases, particularly alkali metal carbonates, and organic bases, particularly tertiary lower alkylamines and pyridines, are suitable as neutralizing agents.

Aminocarbinol compounds of the Formula XIVb:

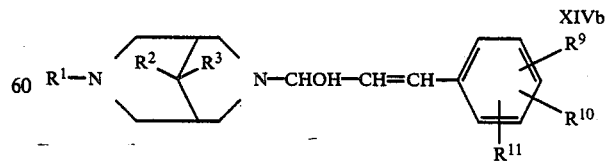

XIVb in which $R^1$, $R^2$, $R^3$, $R^9$, $R^{10}$ and $R^{11}$ have the above meanings, may be formed, for example, by condensing a compound of Formula II with an aldehyde of the Formula XVI:

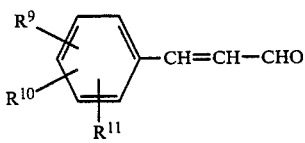

XVI wherein $R^9$, $R^{10}$ and $R^{11}$ have the above meanings, and are advantageously reduced further directly in situ into compounds of Formula Ia according to process variant b.

The reaction of the aldehydes of Formula XVI with the compounds of Formula II may be carried out in accordance with conventional methods for producing aminoalcohols. For instance, the condensation of the aldehyde compounds of Formula XVI with the cyclic amine compounds of Formula II may take place by heating in a polar solvent which is inert under the reaction conditions, for instance, a lower alcohol such as methanol.

The acids of Formula XV and the aldehydes of Formula XVI are known and/or may be produced in a known manner. Similarly, the compounds of Formula III are known and/or may be obtained in a known way.

The starting compounds of Formula III, in which $R^{4'}$ is an optionally substituted benzhydryl group, may be obtained, for instance, by converting the alcoholic hydroxy group in carbinol compounds of Formula XII:

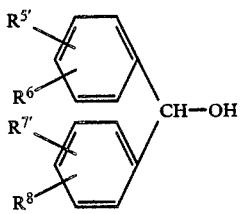

XII in which $R^{5'}$ and $R^{7'}$ have the meanings given above for $R^5$ and $R^7$ except that any free hydroxy groups are provided with a protective group, and $R^6$ and $R^8$ have the above meanings, into an aminolytically cleavable group X in a known manner. In order to introduce a halide group X, the carbinol compounds of Formula XII may, for example, be reacted with the appropriate hydrogen halide. For this purpose the compound of Formula XII is advantageously reacted in an inert organic solvent, e.g., an ether or an aromatic hydrocarbon such as benzene, with gaseous hydrogen halide at room temperature or slightly elevated temperature, optionally in the presence of a drying agent. If the halide group X represents chlorine, it is advantageous, for instance, to add $CaCl_2$ as a drying agent. In order to introduce a sulfonic acid group X, the compounds of Formula XII are advantageously reacted with the appropriate sulfonic acid chloride. The reaction may take place, for instance, in an inert solvent, e.g., a cyclic ether such as tetrahydrofuran or a halogenated hydrocarbon such as dichloromethane at room tempeature.

Compounds of Formula XII may be obtained in a known way be reduction of corresponding benzophenones of Formula XIII:

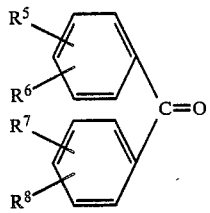

XIII in which $R^5$, $R^6$, $R^7$ and $R^8$ have the above meanings. Examples of suitable reducing agents include boron hydrides such as sodium borohydride, or metallic zinc/caustic soda. The benzophenones of Formula XIII are known and/or may be obtained in a known manner by reacting an appropriately substituted benzonitrile or benzoic acid ester with an appropriately substituted phenyl magnesium halide in a Grignard reaction.

Compounds of Formula XII may also be obtained by reacting appropriately substituted benzaldehydes with appropriately substituted phenyl magnesium halides in a Grignard reaction in a known way to produce carbinol compounds of Formula XII.

Compounds of Formula III in which $R^{4'}$ is an optionally substituted cinnamyl group, may be obtained, for instance, starting from acids of Formula XV or their lower alkyl esters or aldehydes of Formula XVI, by reducing them first to carbinol compounds of Formula XVII,

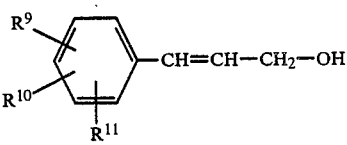

XVII in which $R^9$, $R^{10}$ and $R^{11}$ have the above meanings, and then converting the alcoholic hydroxy group in a known manner into an aminolytically cleavable group X. Suitable reducing agents for reducing the acids of Formula XV or their lower alkyl esters or reducing the aldehydes of Formula XVI to the carbinols of Formula XVII include complex metal hydrides, such as lithium aluminum hydride and in the case of aldehydes also sodium borohydride. In order to introduce a halide group X, the carbinol compounds of Formula XVII may, for instance, be reacted with the appropriate hydrogen halides. For this purpose the compound of Formula XVII is advantageously heated to boiling in an aqueous solution of the hydrogen halide. The introduction of a chloride may also take place by reaction in a known way with thionyl chloride. In order to introduce a sulfonic acid group X, the compounds of Formula XVII are advantageously reacted with the appropriate sulfonic acid chloride. The reaction may take place, for example, in an inert solvent, e.g., a cyclic ether such as tetrahydrofuran or a halogenated hydrocarbon such as dichloromethane at room temperature.

The new compounds of Formula I according to the invention and their pharmacologically acceptable acid addition salts show interesting pharmacological properties, especially properties affecting the cardiovascular system. The compounds are characterized by marked heart rate-lowering effects with a favorable activity profile. Thus the compounds have antiarrhythmic properties as well as bradycardic effects, without adversely affecting the oxygen demand of the heart or the blood pressure.

The heart-affecting properties of the compounds can be demonstated in vitro and in vivo by standard pharmacological test methods.

I. In vitro demonstration of the heart frequency decreasing effect and the antiarrhythmic effect.

The direct influence of the active substances on the heart rate (FRQ) was tested on spontaneously beating, isolated right auricles of male Pirbright-white guinea pigs weighing 250–300 g. In the following Table I the concentration in μmol/l which leads to a decrease in frequency to 75% of the initial value 20 minutes after administration of the test substance is given as FRQ 75.

The antiarrhythmic acitivity of the test substances was demonstrated experimentally by determining the functional refractory period (=FRP) of electrically stimulated (1 Hz) left heart auricles of male Pirbright-white guinea pigs weighing 250–300 g with the help of paired electrical stimulation following the method of Govier (W. C. Govier, J. Pharmacol. Exp. Ther., 148 (1) (1965) 100–05). In the following Table I, the concentration in μmol/l which leads to an extension of the functional refractory period by 25 ms 18 minutes after administration of the substance is given as FRP +25 ms. The example numbers given for the test substances in Table I refer to the following synthesis examples.

TABLE I

| Test substance of Formula I Substance Example No. | Properties affecting the heart. Effective concentration in μmol/l in order to achieve | |
|---|---|---|
| | FRQ 75% | FRP + 25 ms |
| 2 | 4.3 | 4.1 |
| 4 | 1.6 | 3.5 |
| 3 | 1.4 | 3.5 |
| 10 | 2.4 | 4.9 |
| 36 | 0.74 | 4.3 |
| 33 | 0.89 | 7.9 |
| 37 | 1.2 | 8.9 |

II. In vivo experiments on anaesthetized rats.

The effect of the substances on heart frequency and blood pressure during continuous i.v. infusion in anaesthetized rats was determined according to the method of Buschmann et al., (J. Cardiovascular Pharmacol., 2, 777–81 (1980)).

Male Wistar rats (body weight 330 to 370 g) were anaesthetized by i.p. administration of 1.25 g/kg urethane and tracheotomized. Measurements were begun after an equilibration phase of 10 minutes. The initial values were measured in a pre-test phase of 5 minutes. Thereafter, the test substances were administered intravenously dissolved in isotonic sodium chloride solution (optionally with added solubilizer) as a continuous infusion, beginning with the lowest dose. The dose was increased ten-fold every 10 minutes without increasing the infusion volume. The systolic and diastolic blood pressure ($P_s$ and $P_d$) were measured, and from this the mean blood pressure ($P_m$) was determined. At the same time, the heart rate was determined from the interval R-R of the electrocardiogram (ECG). In the following Table II the measured initial values for each test animal group are given for the heart rate (FRQ) and the diastolic blood pressure ($P_d$), together with the values measured at a test substance dose of 10 μmol/kg, and the change in these parameters is calculated in %.

TABLE II

| Influence on heart rate (FRQ) and diastolic blood pressure ($P_d$) | | | | | |
|---|---|---|---|---|---|
| Test substance Example No. | Dose μmol/kg | FRQ min$^{-1}$ | % change FRQ | $P_d$ mm HG | % change $P_d$ |
| Initial values | 0 | 413 | — | 72 | — |
| 17 | 10 | 303 | −27 | 77 | +7 |
| Initial values | 0 | 340 | — | 95 | — |
| 12 | 10 | 249 | −27 | 85 | −11 |
| Initial values | 0 | 405 | — | 64 | — |
| 1 | 10 | 208 | −49 | 71 | +11 |
| Initial values | 0 | 395 | — | 96 | — |
| 5 | 10 | 241 | −39 | 91 | −5 |
| Initial values | 0 | 360 | — | 79 | — |
| 13 | 10 | 196 | −46 | 81 | +3 |

As can be seen from Table II, the test substances reduced the heart frequency, without the diastolic blood pressure being noticeably influenced in the dosage range of frequency reducing effects.

Because of the pharmacological properties described above, particularly the marked heart frequency reducing effects in combination with antiarrhythmic properties, the substances are useful for prophylaxis and treatment of cardiovascular illnesses. Because of their favorable activity profile, the substances are also suitable for the treatment of ischaemically-influenced heart diseases.

The doses to be used may differ individually and naturally vary according to the type of the condition to be treated, the substance used and the manner of administration. For instance, parenteral formulations will generally contain less active substance than oral preparations. In general, however, medicinal forms containing 0.1–10 mg of active substance per individual dose are suitable for administration to larger mammals, in particular humans.

As medicaments, the compounds of Formula I and their physiologically acceptable acid addition salts may be contained with standard pharmaceutical adjuvants in galenic preparations such as tablets, capsules, suppositories or solutions. These galenic preparations may be produced according to known methods using standard solid carrier substances such as lactose, starch or talcum, or liquid diluents such as water, fatty oils or liquid paraffins, and using standard pharmaceutical adjuvants, such as tablet disintegrating agents, solubilizers or preservatives.

The following synthesis and composition examples illustrate the invention in greater detail, witout in any way restricting its scope. If the compounds produced in the following examples are not characterized by their melting points, then they are characterized by their retention times in the gas chromatograph. Retention time measurements were performed under the following conditions:

Gas chromatograph used: Hewlett Packard type 5750G Gas Chromatograph,
Detector used: flame ionization detector,
Detector temperature: 300° C.,
Injection temperature: 290° C.,
Heating rate from 80° to 280° C./min.
Types of columns used:
  Column type A*: length 30 m, internal diameter 0.75 mm, methyl silicone inner coating with a film thickness of 1 μm; carrier gas nitrogen, flow rate 12 ml/min.

*=column type SPB1 from the company Supelco

Column type B: length 6 foot, internal diameter ⅛ inch, filled with an SiO$_2$-based filler with a grain size of 80/100*; carrier gas nitrogen, flow rate 22 ml/min.
**=column type 3% OV1 from the company Supelco
***=Supelcoport ® from the company Supelco

EXAMPLE 1

7-diphenylmethyl-3-butyl-9,9-dimethyl-3,7-diazabicyclo[3,3,1]nonane.

4.3 g 3-butyl-9,9-dimethyl-3,7-diazabicyclo[3,3,1]nonane were allowed to react in 50 ml dimethylformamide together with 6.06 g diphenylmethyl bromide and 4.2 g potassium carbonate at room temperature for 12 hours. To work up the reaction mixture, it was filtered, and the filtrate containing the title compound was concentrated at reduced pressure.

For further purification the residue containing the crude title compound was dissolved in an aqueous citric acid solution, the title compound dissolving as a citric acid salt. The solution was washed with diethyl ether and subsequently rendered alkaline by addition of dilute sodium hydroxide; the title compound being released again as a base, which was extracted with diethyl ether. After drying the ether extract over magnesium sulfate, the etherial solution was filtered and the ether distilled off. 3.9 g 7-diphenylmethyl-3-n-butyl-9,9-dimethyl-3,7-diazabicyclo[3,3,1]nonane were obtained as an oleaginous base.

Gas chromatography: column B, retention time 6,82 min.

EXAMPLE 2:

7-diphenylmethyl-3-cyclohexylmethyl-9,9-tetramethylene-3,7-diazabicyclo[3,3,1]nonane.

1.5 g 3-cyclohexylmethyl-9,9-tetramethylene-3,7-diazabicyclo[3,3,1]nonane were dissolved in 30 ml tetrahydrofuran and 3.64 ml of a 1.5 molar solution of n-butyl lithium in hexane were added at 0° C. The reaction mixture was maintained at this temperature for 1 hour and then 1.47 g diphenylmethyl bromide dissolved in 20 ml tetrahydrofuran were added in drops to the reaction mixture at 0° C. The reaction mixture was heated to room temperature while stirring and the mixture was stirred for a further 12 hours.

In order to work up the reaction mixture, dilute aqueous citric acid solution was first added to it, and it was then worked up by acid/base separation according to the method of Example 1. 1.7 g 7-diphenylmethyl-3-cyclohexylmethyl-9,9-tetramethylene-3,7-diazabicyclo[3,3,1]nonane were obtained as an oleaginous base.

Gas chromatography: column A, retention time: 21.84 min.

EXAMPLE 3:

7-diphenylmethyl-3-cyclopropylmethyl-9,9-dimethyl-3,7-diazabicyclo[3,3,1]nonane.

1 g 3-cyclopropylmethyl-9,9-dimethyl-3,7-diazabicyclo[3,3,1]nonane was dissolved in 25 ml absolute tetrahydrofuran, and 0.2 g lithium amide was added to the solution and stirred for 1 hour at 60° C. and then left to cool. After cooling, a solution of 3 g diphenylmethyl bromide in 25 ml absolute tetrahydrofuran was added slowly in drops, and the reaction mixture was stirred further for 90 min at a temperature of 40° C. Then the reaction mixture was acidified with aqueous citric acid solution and worked up as described in Example 1. 1.5 g 7-diphenylmethyl-3-cyclopropylmethyl-9,9-dimethyl-3,7-diazabicyclo[3,3,1]nonane were obtained as an oleaginous base.

Gas chromatography: column A, retention time: 14.66 min.

For conversion into the hydrogen tartrate 1.5 g of the basic oleaginous title compound obtained above were dissolved in 10 ml acetone were added to the solution while stirring. The resulting reaction solution was highly concentrated in a rotary evaporator and then allowed to cool. The precipitate formed on cooling was filtered out and dried at 50° C. in a vacuum drier. 1.2 g 7-diphenylmethyl-3-cyclopropylmethyl-9,9-dimethyl-3,7-diazabicyclo[3,3,1]nonane-monohydrogen tartrate were obtained with a melting point of 216°-217° C.

EXAMPLE 4:

7-[bis-(4-fluorophenyl)methyl]-3-cyclopropylmethyl-9,9-dimethyl-3,7-diazabicyclo[3,3,1]nonane.

3.5 g 3-cyclopropylmethyl-9,9-dimethyl-3,7-diazabicyclo[3,3,1]nonane were dissolved in 25 ml dimethylformamide, and 0.8 g lithium amide were added to the solution. The reaction mixture was then maintained at a temperature of 60° C. for one hour and subsequently allowed to cool. After cooling, a solution of 8 g bis-(4-fluorophenyl)methyl chloride in 10 ml dimethylformamide was added in drops, and the reaction mixture was stirred for a further 4 hours at 40° C. Then aqueous citric acid solution was added to the reaction mixture, and the mixture was worked up as described in Example 1. 5.8 g 7-[bis-(4-fluorophenyl)methyl]-3-cyclopropylmethyl-9,9-dimethyl-3,7diazabicyclo[3,3,1-]nonane were obtained as an oleaginous base.

Gas chromatography: column A, retention time: 14.24 min.

EXAMPLE 5:

7-cinnamyl-3-n-butyl-9,9-dimethyl-3,7-diazabicyclo[3,3,1]nonane.

1.5 g 3-butyl-9,9-dimethyl-3,7-diazabicyclo[3,3,1]nonane were dissolved in 20 ml dichloromethane and a solution of 1.2 g cinnamyl chloride in 20 ml dichloromethane was added to the solution. The reaction mixture was allowed to react for one hour at room temperature.

For working up and further purification the residue containing the crude title compound was dissolved in aqueous citric acid solution, the title compound dissolving as a citric acid salt. In order to separate non-basic impurities, the solution was extracted with diethyl ether. Subsequently the aqueous solution was rendered alkaline with dilute aqueous sodium hydroxide soltuion, the title compound again being released as a base which was extracted with diethyl ether. After drying the ether extract over magnesium sulfate, the ethereal solution was filtered and the ether distilled off. 1.4 g 7-cinnamyl-3-n-butyl-9,9-dimethyl-3,7-diazabicyclo[3,3,1]nonane were obtained as an oleaginous base.

Gas chromatography: column B, retention time: 6.21 min.

EXAMPLE 6:

7-cinnamyl-3-isobutyl-9,9-dimethyl-3,7-diazabicyclo[3,3,1]nonane.

3 g 3-isobutyl-9,9-dimethyl-3,7-diazabicyclo[3,3,1]nonane were dissolved in 25 ml dimethylformamide, and 0.6 g lithium amide were added to the solution, which was subsequently stirred further for 60 minutes at a temperature of 60° C. After the solution was cooled, a solution of 4.1 g cinnamyl chloride in 25 ml dimethylformamide was added in drops, and the reaction mixture was stirred for a further 2 hours at 40° C.

For working up, the solvent was distilled off; aqueous citric acid solution was added to the residue containing the title compound, and the solution was worked up as described in Example 5. 3.1 g 7-cinnamyl-3-isobutyl-9,9-dimethyl-3,7-diazabicyclo[3,3,1]nonane were obtained as an oleaginous base.

Gas chromatography: column A, retention time 12.45 min.

EXAMPLE 7:

7-cinnamyl-3-benzyl-9,9-dimethyl-3,7-diazabicyclo[3,3,1]nonane.

(A) 3.9 g cinnamic acid chloride were dissolved in 20 ml dichloromethane, and to this solution a solution of 5.5 g 3-benzyl-9,9-dimethyl-3,7-diazabicyclo[3,3,1]nonane in 10 ml dichloromethane was added with ice cooling. Subsequently the reaction mixture was stirred for 3 hours at room temperature. Then, for working up, the solvent was distilled off and the residue containing the 7-cinnamyl-3-benzyl-9,9-dimethyl-3,7-diazabicyclo[3,3,1]nonane which had formed was dissolved in water. To remove non-basic fractions, extraction was carried out using ethyl acetate. Then the aqueous phase was made alkaline with dilute sodium hydroxide solution, and the reaction product was extracted with ethyl acetate. The ethyl acetate extract was dried over magnesium sulfate, filtered, and the solvent was distilled off. 5 g 7-cinnamoyl-3-benzyl-9,9-dimethyl-3,7-diazabicyclo[3,3,1]nonane were obtained as a residue.

Gas chromatography: column A, retention time: 19.96 min.

(B) 0.8 g of the above product were dissolved in 20 ml toluene, and to the solution 0.9 ml of a 3.4 molar solution of sodium-bis-(2-methoxyethoxy)dihydroaluminate (Red-Al ®) in toluene were added in drops at room temperature. Subsequently, the reaction mixture was stirred for a further 12 hours. In order to work up the reaction mixture containing the title compound, 5 ml water, 5 ml 20% aqueous sodium hydroxide and 15 more ml water were added one after the other. The resulting aluminate precipitate which formed was removed by filtration, and the filtrate was extracted using ethyl acetate. After drying over magnesium sulfate and concentrating the solution, 0.5 g 7-cinnamyl-3-benzyl-9,9-dimethyl-3,7-diazabicyclo[3,3,1]nonane were obtained as an oily residue.

Gas chromatography: column A, retention time 15.39 min.

EXAMPLE 8:

7-[1-(4'-hydroxyphenyl)-1-phenylmethyl]-3-hexyl-9,9-pentamethylene-3,7-diazabicyclo[3,3,1]nonane.

8 ml 57% hydriodic acid were dropped slowly into 1.2 g 7-[1-(4'-methoxyphenyl)-1-phenylmethyl]-3-hexyl-9,9-pentamethylene-3,7-diazabicyclo[3,3,1]nonane in 4 ml acetic anhydride (see Example 32). The mixture was then heated for 4 hours under reflux. After cooling, the reaction mixture was carefully poured onto ice water, and an acid/base separation was carried out as described in Example 1. The reaction product was extracted from the alkaline-aqueous phase using methylene chloride. The methylene chloride extract was dried over magnesium sulfate and the solvent distilled off. The 7-[1-(4'-hydroxyphenyl)-1-phenylmethyl]-3-hexyl-9,9-pentamethylene-3,7-diazabicyclo[3,3,1]nonane was isolated from the residue by means of bulb tube distillation at reduced pressure.

Gas chromatography: column A, retention time:

EXAMPLE 9:

7-(4'-nitrocinnamyl)-3-cyclopropylmethyl-9,9-tetramethylene-3,7-diazabicyclo[3,3,1]nonane.

0.8 g p-nitrocinnamaldehyde were added to a solution of 1.24 g 3-cyclopropylmethyl-9,9-tetramethylene-3,7-diazabicyclo[3,3,1]nonane in 50 ml methanol, and the reaction mixture was allowed to react for 1 hour at room temperature. Then 0.8 g sodium borohydride were added slowly to the reaction mixture which contained the 7-(4'-nitro-α-hydroxycinnamyl)-3-cyclopropylmethyl-9,9-tetramethylene-3,7-diazabicyclo[3,3,1]nonane which had formed, and the reaction mixture was allowed to react for a further 2 hours at room temperature. Subsequently the solvent was distilled off, and the residue was dissolved in methylene chloride. The methylene chloride solution was washed with water, dried over magnesium sulfate and concentrated. The 7-(4'-nitrocinnamyl)-3-cyclopropylmethyl-9,9-tetramethylene-3,7-diazabicyclo[3,3,1]nonane was isolated from the residue by bulb tube distillation at reduced pressure.

Gas chromatography: column A, retention time: 19.92 min.

The compounds of Formula I listed in the following Tables 1a and 1b may also be obtained by methods analogous to those described in the foregoing examples.

TABLE 1a

| Example No. | $R^4$ = diphenylmethyl substituted by $R^1$ | $R^2$ | $R^3$ | $R^5$ | $R^6$ | $R^7$ | $R^8$ | Retention Time (RT) of the base in min. Column (A) or (B) | Gas Chromatograph Melting Point in °C. salt form |
|---|---|---|---|---|---|---|---|---|---|
| 10 | $(CH_3)_2CH-CH_2-$ | $CH_3-$ | $CH_3-$ | H | H | H | H | RT: 14.29 (A) | |
| 11 | $(CH_3)_2CH-CH_2-$ | $CH_3-$ | $CH_3-$ | 4-F | H | 4-F | H | RT: 14.38 (A) | |
| 12 | $n\text{-}C_4H_9-$ | $n\text{-}C_3H_7-$ | $n\text{-}C_3H_7-$ | H | H | H | H | RT: 16.90 (A) | |
| 13 | $n\text{-}C_4H_9-$ | $CH_3-$ | $CH_3-$ | 4-F | H | 4-F | H | | B: 82 |
| 14 | $(CH_3)_2CH-$ | $-(CH_2)_4-$ | | H | H | H | H | RT: 15.34 (A) | B: 67-68 |
| 15 | $(CH_3)_2CH-$ | $-(CH_2)_4-$ | | 4-F | H | 4-F | H | RT: 15.27 (A) | B: 102 |
| 16 | cyclohex-$CH_2-$ | $-(CH_2)_4-$ | | 4-F | H | 4-F | H | RT: 19.99 (A) | |
| 17 | cyclohex-$CH_2-$ | $CH_3-$ | $CH_3-$ | H | H | H | H | RT: 17.41 (A) | |
| 18 | $(CH_3)_2CH-CH_2-$ | $-(CH_2)_4-$ | | H | H | H | H | RT: 16.62 (A) | B: 101 |
| 19 | $(CH_3)_2CH-CH_2-$ | $-(CH_2)_4-$ | | 4-F | H | 4-F | H | RT: 15.47 (A) | |
| 20 | cycloprop-$CH_2-$ | $-(CH_2)_4-$ | | H | H | H | H | RT: 18.23 (A) | 1HBR: 180 |
| 21 | cycloprop-$CH_2-$ | $-(CH_2)_4-$ | | 4-F | H | 4-F | H | RT: 16.22 (A) | B: 103 |
| 22 | benz- | $-(CH_2)_4-$ | | H | H | H | H | RT: 23.27 (A) | |

TABLE 1a-continued

| Example No. | R¹ (R⁴ = diphenylmethyl substituted by) | R² | R³ | R⁵ | R⁶ | R⁷ | R⁸ | Gas Chromatograph Retention Time (RT) of the base in min. Point in °C. Column (A) or (B) | Melting Point in °C. salt form |
|---|---|---|---|---|---|---|---|---|---|
| 23 | benz- | | —(CH$_2$)$_4$— | 4-F | H | 4-F | H | RT: 22.04 (A) | |
| 24 | cycloprop-CH$_2$— | CH$_3$— | CH$_3$— | H | H | 4-Cl | H | RT: 15.87 (A) | |
| 25 | cycloprop-CH$_2$— | CH$_3$— | CH$_3$— | H | H | 4-CH$_3$ | H | RT: 15.11 (A) | |
| 26 | cycloprop-CH$_2$— | CH$_3$— | CH$_3$— | 4-Cl | H | 4-Cl | H | RT: 17.98 (A) | |
| 27 | benz- | | —(CH$_2$)$_5$— | H | H | 4-Cl | H | RT: 29.01 (A) | |
| 28 | benz- | | —(CH$_2$)$_5$— | 4-Cl | H | 4-Cl | H | RT: 36.88 (A) | |
| 29 | benz- | | —(CH$_2$)$_5$— | H | H | 4-CH$_3$ | H | RT: 25.00 (A) | |
| 30 | n-C$_6$H$_{13}$— | | —(CH$_2$)$_5$— | H | H | 3-CH$_3$ | 4-CH$_3$ | RT: 23.48 (A) | |
| 31 | n-C$_6$H$_{13}$— | | —(CH$_2$)$_5$— | H | H | 4-CF$_3$ | H | RT: 18.35 (A) | |
| 32 | n-C$_6$H$_{13}$— | | —(CH$_2$)$_5$— | H | H | 4-OCH$_3$ | H | RT: 17.43 (A) | | benz = benzyl;
cyclohex = cyclohexyl;
cycloprop = cyclopropyl;
B = base;
HBr = hydrobromide TABLE 1b

| Example No. | R¹ | R² | R³ | R⁹ (R⁴ = cinnamyl substituted by) | R¹⁰ | R¹¹ | Gas Chromatograph Retention Time (RT) of the base in min. Column (A) or (B) |
|---|---|---|---|---|---|---|---|
| 33 | cycloprop-CH$_2$— | CH$_3$— | CH$_3$— | H | H | H | RT: 13.15 (A) |
| 34 | (CH$_3$)$_2$CH— | —(CH$_2$)$_4$— | | H | H | H | RT: 13.87 (A) |
| 35 | (CH$_3$)$_2$CH—CH$_2$— | —(CH$_2$)$_4$— | | H | H | H | RT: 14.81 (A) |
| 36 | cycloprop-CH$_2$— | —(CH$_2$)$_4$— | | H | H | H | RT: 7.14 (B) |
| 37 | benz- | —(CH$_2$)$_4$— | | H | H | H | RT: 18.91 (A) |
| 38 | cyclohex-CH$_2$— | CH$_3$— | CH$_3$— | H | H | H | RT: 15.04 (A) |
| 39 | n-C$_4$H$_9$— | CH$_3$— | CH$_3$— | 2-OCH$_3$ | H | H | RT: 13.62 (A) |
| 40 | n-C$_6$H$_{13}$— | —(CH$_2$)$_5$— | | 4-Cl | H | H | RT: 18.82 (A) |
| 41 | n-C$_6$H$_{13}$— | —(CH$_2$)$_5$— | | 3-Cl | 4-Cl | H | RT: 21.69 (A) |
| 42 | n-C$_6$H$_{13}$— | —(CH$_2$)$_5$— | | 4-NO$_2$ | H | H | RT: 23.91 (A) |
| 43 | cycloprop-CH$_2$— | —(CH$_2$)$_4$— | | 3-CH$_3$ | H | H | RT: 15.99 (A) |
| 44 | cycloprop-CH$_2$— | —(CH$_2$)$_4$— | | 4-CF$_3$ | H | H | RT: 15.65 (A) |
| 45 | cycloprop-CH$_2$— | —(CH$_2$)$_4$— | | 3,4,5-tri-OCH$_3$ | | | RT: | benz = benzyl;
cycloprop = cyclopropyl;
cyclohex = cyclohexyl

The starting materials used were produced in accordance with the following general operating directions:

(A) General operating directions for producing 3,7-disubstituted-2,4,6,8-tetraoxo-3,7-diazabicyclo[3,3,1]nonane compounds of Formula VII by reacting 2,4,6,8-tetraoxo-3,7-diazabicyclo[3,3,1]nonane compounds of Formula V with benzyl halides of Formula VI.

(a) Reaction of N-monosubstituted compounds of Formula V in which R¹ is other than H.

A mixture of 0.1 mole of the imide compound of Formula V, 0.2 mole potassium carbonate and 0.15 mole benzyl halide of Formula VI in 390 ml dimethylformamide was heated for 3 to 7 hours under reflux. Then the precipitate of inorganic salts which formed was filtered out, and the clear solution was concentrated to dryness. The remaining residue was dissolved in water and ethyl acetate. The organic solution was separated, washed twice with water, dried over magnesium sulfate, filtered and concentrated. If the resulting tetraoxo compounds of Formula VII already appear in crystalline form, simple recrystallization is sufficient for further purification. Otherwise, it may be necessary to purify the obtained crude product by column chromatography over silica gel or aluminum oxide using ethyl acetate/hexane mixtures as eluants.

(b) Reaction of compounds of Formula V in which R¹ represents hydrogen.

In order to disubstitute the compounds of Formula V in which R¹=H with benzyl halides of Formula VI, the foregoing general operating directions for monosubstitution of the compounds of Formula V in which R¹ is other than H, are modified. Instead of the reaction mixture given above, a mixture of 0.1 mole of the tetraoxo compound of Formula V, 0.25 mole potassium carbonate and 0.3 mole benzyl halide of Formula VI in 300 ml dimethylformamide is used.

The following compounds, given in Table A, were produced according to the foregoing general operating directions.

TABLE A

Compounds of Formula VII

| Substance No. | R¹ | R² | R³ | R¹¹ | Remarks MP = melting point in °C. |
|---|---|---|---|---|---|
| A1 | n-C$_4$H$_9$— | CH$_3$— | CH$_3$— | benz | MP: 110 |
| A2 | n-C$_4$H$_9$— | n-C$_3$H$_7$— | n-C$_3$H$_7$— | benz | oil* |
| A3 | cyclohex-CH$_2$— | CH$_3$— | CH$_3$— | benz | MP: 129–131 |
| A4 | cycloprop-CH$_2$— | CH$_3$— | CH$_3$— | benz | oil* |
| A5 | (CH$_3$)$_2$CH—CH$_2$— | CH$_3$— | CH$_3$— | benz | oil* |
| A6 | (CH$_3$)$_2$CH— | —(CH$_2$)$_4$— | | benz | oil* |

TABLE A-continued

Compounds of Formula VII

| Substance No. | $R^1$ | $R^2$ | $R^3$ | $R^{11}$ | Remarks MP = melting point in °C. |
|---|---|---|---|---|---|
| A7 | cycloprop-$CH_2$— | | —$(CH_2)_4$— | benz | oil* |
| A8 | $(CH_3)_2CH$—$CH_2$— | | —$(CH_2)_4$— | benz | oil* |
| A9 | cyclohex-$CH_2$— | | —$(CH_2)_4$— | benz | oil* |
| A10 | benz- | | —$(CH_2)_4$— | benz | oil* |
| A11 | n-$C_6H_{13}$— | | —$(CH_2)_5$— | benz | oil* |
| A12 | benz- | $CH_3$— | $CH_3$— | benz | MP: 155–157 |
| A13 | benz- | | —$(CH_2)_5$— | benz | MP: 150–154 | benz = benzyl; cyclohex = cyclohexyl; cycloprop = cyclopropyl
oil* = was processed further as an oil (B) General opeating directions for reducing 2,4,6,8-tetraoxo-3,7-diazabicyclo[3,3,1]nonane compounds of Formula VII to 3,7-diazabicyclo[3,3,1]nonane compounds of Formula IV.

0.1 mole lithium aluminum hydride in 100 ml of a solution of 70 ml absolute tetrahydrofuran and 30 ml absolute toluene were heated to an oil bath temperature of 80° C. in a three-necked flask. Then 0.025 mole of the tetraoxo compound in 100 ml of a 70/30 mixture of tetrahydrofuran/toluene were slowly added dropwise. The reaction mixture was allowed to react for 2 to 4 hours at 120° C. Then it was hydrolyzed under basic conditions and extracted with methylene chloride. The organic phase was separated, dried over magnesium sulfate and concentrated. The 3,7-diazabicyclo[3,3,1]nonane compounds which formed crystallized out or were separated by bulb tube distillation at reduced pressure.

The 3,7-diazabicyclo[3,3,1]nonane compounds of Formula IV given in the following Table B were produced according to these general operating directions for reduction by means of lithium aluminum hydride.

TABLE B

| Substance IV No. | $R^1$ | $R^2$ | $R^3$ | $R^{11}$ | Remarks BP = boiling pt. °C. (0.01 Torr) MP = melting pt. | Gas Chromatograph Retention Time (RT) in min. Column (A) or (B) |
|---|---|---|---|---|---|---|
| B1 | n-$C_4H_9$— | $CH_3$— | $CH_3$— | benz | BP: 170 | |
| B2 | n-$C_4H_9$— | n-$C_3H_7$— | n-$C_3H_7$— | benz | BP: 200 | |
| B3 | cyclohex-$CH_2$— | $CH_3$— | $CH_3$— | benz | BP: 170 | RT: 13.23 (A) |
| B4 | cycloprop-$CH_2$— | $CH_3$— | $CH_3$— | benz | | RT: 11.54 (A) |
| B5 | $(CH_3)_2CH$—$CH_2$— | $CH_3$— | $CH_3$— | benz | | RT: 9.85 (B) |
| B6 | $(CH_3)_2CH$— | | —$(CH_2)_4$— | benz | | RT: 10.84 (A) |
| B7 | cycloprop-$CH_2$— | | —$(CH_2)_4$— | benz | | RT: 6.29 (B) |
| B8 | $(CH_3)_2CH$—$CH_2$— | | —$(CH_2)_4$— | benz | | RT: 12.67 (A) |
| B9 | cyclohex-$CH_2$— | | —$(CH_2)_4$— | benz | MP: 58 | RT: 7.23 (B) |
| B10 | benz- | | —$(CH_2)_4$— | benz | MP: 54 | RT: 7.24 (B) |
| B11 | n-$C_6H_{13}$— | | —$(CH_2)_5$— | benz | | RT: 14.70 (A) |
| B12 | benz- | $CH_3$— | $CH_3$— | benz | MP: 58 | RT: 13.47 (A) |
| B13 | benz- | | —$(CH_2)_5$— | benz | MP: 60 | RT: 16.66 (A) | benz = benzyl; cyclohex = cyclohexyl; cycloprop = cyclopropyl (C) General operating directions for debenzylating 3,7-disubstituted 3,7-diazabicyclo[3,3,1]nonane compounds of Formula IV to N-monosubstituted 3,7-diazabicyclo[3,3,1]nonane compounds of Formula II.

0.2 mole of a compound of Formula IV were dissolved in 600 ml ethanol with the addition of 5 ml glacial acetic acid, and 10 g palladium/carbon catalyst were added to the solution. The reaction mixture was hydrogenated at room temperature under a hydrogen pressure of 5 atmospheres for approximately 6 hours. After hydrogenation had ended, the solution was separated from the catalyst and concentrated. The compounds of Formula II which formed could be further purified with the aid of bulb tube distillation at reduced pressure.

The 3,7-diazabicyclo[3,3,1]nonane compounds of Formula II listed in the following Table C were produced according to the foregoing general directions for debenzylation.

TABLE C

Compounds of Formula II

| Substance IV No. | $R^1$ | $R^2$ | $R^3$ | Remarks BP = boiling point in °C. (0.01 Torr) MP = melting point in °C. | Gas Chromatigraph Retention Time (RT) in min. Column (A) or (B) |
|---|---|---|---|---|---|
| C1 | n-$C_4H_9$— | $CH_3$— | $CH_3$— | BP: 145 | |
| C2 | n-$C_4H_9$— | n-$C_3H_7$— | n-$C_3H_7$— | BP: 220(1.5 Torr) | |
| C3 | cyclohex-$CH_2$— | $CH_3$— | $CH_3$— | N.D. | |
| C4 | cycloprop-$CH_2$— | $CH_3$— | $CH_3$— | | RT: 7.74 (A) |
| C5 | $(CH_3)_2CH$—$CH_2$— | $CH_3$— | $CH_3$— | | RT: 5.78 (B) |
| C6 | cycloprop-$CH_2$— | | —$(CH_2)_4$— | 2WS, MP: 75 | RT: 4.59 (B) |
| C7 | $(CH_3)_2CH$— | | —$(CH_2)_4$— | 2WS, MP: 115 | RT: 8.71 (A) |
| C8 | $(CH_3)_2CH$—$CH_2$— | | —$(CH_2)_4$— | | RT: 9.32 (A) |

TABLE C-continued

Compounds of Formula II

| Substance IV No. | R$^1$ | R$^2$ | R$^3$ | BP = boiling point in °C. (0.01 Torr) MP = melting point in °C. | Gas Chromatigraph Retention Time (RT) in min. Column (A) or (B) |
|---|---|---|---|---|---|
| C9  | cyclohex-CH$_2$— |       | —(CH$_2$)$_4$— | 1HCl, MP: 185 | RT: 11.83 (A) |
| C10 | benz-            |       | —(CH$_2$)$_4$— |               | RT: 12.38 (A) |
| C11 | n-C$_6$H$_{13}$— |       | —(CH$_2$)$_5$— |               | RT: 11.58 (A) |
| C12 | benz-            | CH$_3$— CH$_3$— |          | BP: 180       |               |
| C13 | benz-            |       | —(CH$_2$)$_5$— |               | RT: 12.62 (A) | benz = benzyl; cyclohex = cyclohexyl; cycloprop = cyclopropyl; WS = hydrogen tartrate; HCl = hydrochloride; N.D. = not determined, processed without further purification.

EXAMPLE I:

Tablets containing 7-diphenylmethyl-3-cyclopropylmethyl-9,9-dimethyl-3,7-diazabicyclo[3,3,1]nonane monohydrogen tartrate.

Tablets were produced having the following composition per tablet:
7-diphenylmethyl-3-cyclopropylmethyl-9,9-dimethyl-3,7-diazabicyclo[3,3,1]nonane monohydrogen tartrate 20 mg
Cornstarch 60 mg
Lactose 135 mg
Gelatine (as 10% solution) 6 mg The active substance, the cornstarch and the lactose were thickened with the 10% gelatine solution. The paste was ground, and the resulting granules were placed on a suitable tray and dried. The dried granules were passed through a pulverizer and mixed in a mixer with the following additional adjuvants:
Talcum 5 mg
Magnesium stearate 5 mg
Cornstarch 9 mg
and then pressed into 240 mg tablets.

EXAMPLE II:

Tablets containing 7-cinnamyl-3-isobutyl-9,9-dimethyl-3,7-diazabicyclo[3,3,1]nonane.

Tablets were produced having the following composition per tablet:
7-cinnamyl-3-isobutyl-9,9-dimethyl-3,7-diazabicyclo[3,3,1]nonane 20 mg
Cornstarch 60 mg
Lactose 135 mg
Gelatine (as 10% solution) 6 mg The active substance, the cornstarch and the lactose were thickened with the 10% gelatine solution. The paste was ground, and the resulting granules were placed on a suitable tray and dried. The dried granules were passed through a pulverizer and mixed in a mixer with the following additional adjuvants:
Talcum 5 mg
Magnesium stearate 5 mg
Cornstarch 9 mg
and then pressed into 240 mg tablets.

The foregoing description and examples have been set forth merely to illustrate the invention and are not intended to be exclusive. Since modifications of the described embodiments incorporating the spirit and substance of the invention may occur to persons skilled in the art, the scope of the invention should be limited solely with reference to the appended claims and equivalents.

What is claimed is:

1. A 3,7-diazabicyclo[3,3,1]nonane compound corresponding to the Formula I:

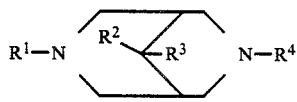

wherein
R$^1$ is an alkyl group with 1–6 carbon atoms, a cycloalkylalkyl group with 4–9 carbon atoms or a benzyl group,
R$^2$ is lower alkyl,
R$^3$ is lower alkyl, or
R$^2$ and R$^3$ together form an alkylene chain with 3–6 carbon atoms, and
R$^4$ represents a cinnamyl group of Formula b:

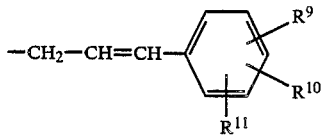

wherein
R$^9$ is hydrogen, halogen, lower alkyl, lower alkoxy or hydroxy,
R$^{10}$ is hydrogen, halogen, lower alkoxy, lower alkyl, hydroxy or, if R$^9$ is hydrogen, R$^{10}$ may also be trifluoromethyl or nitro, and
R$^{11}$ is hydrogen, or, if R$^9$ and R$^{10}$ are lower alkoxy, R$^{11}$ may also be lower alkoxy,
or an acid addition salt thereof.

2. A compound according to claim 6, wherein R$^1$ is an alkyl group with 1–6 carbon atoms or a cycloalkylalkyl group with 4–9 carbon atoms.

3. A compound according to claim 2, wherein said cycloalkylalkyl group contains 4–7 carbon atoms.

4. A compound according to claim 1, wherein R$^{11}$ represents hydrogen.

5. A pharmaceutical composition comprising an effective heart activity affecting amount of a 3,7-diazabicyclo[3,3,1]nonane compound according to claim 1, and a conventional pharmaceutical adjuvant or carrier.

* * * * *